United States Patent
Ursella et al.

(10) Patent No.: US 11,620,742 B2
(45) Date of Patent: Apr. 4, 2023

(54) COMPUTER IMPLEMENTED METHODS FOR TRAINING OR USING A SOFTWARE INFRASTRUCTURE BASED ON MACHINE LEARNING TECHNIQUES

(71) Applicant: MICROTEC S.R.L., Bressanone (IT)

(72) Inventors: Enrico Ursella, Mestre (IT); Enrico Vicario, Martellago (IT); Federico Giudiceandrea, Bressanone (IT)

(73) Assignee: MICROTEC S.R.L., Bressanone (IT)

( * ) Notice: Subject to any disclaimer, the term of this patent is extended or adjusted under 35 U.S.C. 154(b) by 409 days.

(21) Appl. No.: 16/928,385

(22) Filed: Jul. 14, 2020

(65) Prior Publication Data
US 2021/0019873 A1 Jan. 21, 2021

(30) Foreign Application Priority Data
Jul. 15, 2019 (IT) .................. 102019000011778

(51) Int. Cl.
G06T 7/00 (2017.01)
G06N 20/00 (2019.01)
G01N 23/046 (2018.01)

(52) U.S. Cl.
CPC ......... *G06T 7/0004* (2013.01); *G01N 23/046* (2013.01); *G06N 20/00* (2019.01);
(Continued)

(58) Field of Classification Search
CPC . G06T 2207/10081; G06T 2207/20084; G06T 2207/20081; G06T 2207/10072;
(Continued)

(56) References Cited

U.S. PATENT DOCUMENTS

2016/0139977 A1* 5/2016 Ashani .................. G06N 3/08
714/26
2018/0113083 A1* 4/2018 Van Dael ............. G01N 23/046
(Continued)

FOREIGN PATENT DOCUMENTS

| CN | 101542526 A | * | 9/2009 | ........... G06T 7/0024 |
| EP | 3220143 A1 | * | 9/2017 | ........... G01N 23/046 |
| EP | 3916378 A1 | * | 12/2021 | ........... G06K 9/2027 |

OTHER PUBLICATIONS

Volume Segmentation and Analysis of Biological Materials Using SuRVoS (Super-region Volume Segmentation) Workbench—Aug. 23, 2017 (Year: 2017).*

(Continued)

*Primary Examiner* — Nizar N Sivji
(74) *Attorney, Agent, or Firm* — Pearne & Gordon LLP; Michelle E. Tochtrop

(57) ABSTRACT

Computer implemented method for training a software infrastructure based on machine learning techniques and intended for analysis of data obtained from a three-dimensional tomographic inspection of objects of a predetermined type, such as logs, with the aim of determining information about internal characteristics of interest of the self-same objects, wherein, once a training set comprising a plurality of objects of the same predetermined type has been selected, for each object the software infrastructure is supplied with training input data and corresponding training output data, which are processed by the software infrastructure for setting internal processing parameters of the software infrastructure which correlate the training input data with the training output data; where the training input data comprise data obtained from a three-dimensional tomographic inspection of the object, and the training output data comprise information about internal characteristics of interest assessed at internal points of the object, and where the information about the internal char- (Continued)

acteristics of interest is at least partly assessed at real internal points of the object, previously made accessible by cutting or breaking the object.

22 Claims, 2 Drawing Sheets

(52) U.S. Cl.
CPC ............... *G01N 2223/419* (2013.01); *G06T 2207/10072* (2013.01)

(58) Field of Classification Search
CPC ........ G06T 7/0004; G06T 2207/30161; G06N 3/0454; G06N 3/08; G06N 20/00; G06N 3/02; G06N 3/0427; G06N 5/048; G01N 23/046; G01N 2223/419; G01N 33/46
See application file for complete search history.

(56) References Cited

U.S. PATENT DOCUMENTS

| | | | |
|---|---|---|---|
| 2019/0147371 A1* | 5/2019 | Deo | G06N 20/20 706/12 |
| 2019/0265175 A1* | 8/2019 | Schönfeld | H05G 1/54 |
| 2020/0085382 A1* | 3/2020 | Taerum | A61B 5/7267 |

OTHER PUBLICATIONS

Volume Segmentation and Analysis of Biological Materials Using SuRVoS (Super-region Volume Segmentation) Workbench (Year: 2017).*

Giudiceandrea, F., et al., "A High Speed CT Scanner For The Sawmill Industry", In Proceedings of the 17th International non destructive testing and evaluation of wood symposium, Sep. 2011, pp. 14-16.

Rais, A., et al., "The Use of the First Industrial X-Ray CT Scanner Increases the Lumber Recovery Value: Case Study an Visually Strength-Graded Douglas Fir-Timber", Annals of Forest Science, 2017, vol. 74, No. 28, pp. 1-9.

Berglund, A., et al., "Improved Log Rotation Using Information From a Computed Tomography Scanner", Computers and Electronics in Agriculture, 2013, vol. 90, pp. 152-158.

Stangle, S. et al., "Potentially Increased Sawmill Yield From Hardwoods Using X-Ray Computed Tomography For Knot Detection", Annals of Forest Science, Springer Verlag/EDP Sciences, 2015, vol. 72, No. 1, pp. 57-65.

Andreu, JP, et al., "Modeling of Internal Defects in Logs for Value Optimization Based on Industrial CT Scanning", Fifth International Conference on Image Processing and Scanning of Wood—Proceedings, Mar. 23-26, 2003, pp. 141-150.

Breinig, L., et al., "Measurement of Knot Width in CT Images of Norway Spruce (*Picea abies* [L.]Karst.)—Evaluating the Accuracy of an Image Analysis Method", Computers and Electronics in Agriculture, vol. 85, 2012, pp. 149-156.

Fredriksson, M., et al., "Knot Detection in Computed Tomography Images of Partially Dried Jack Pine (*Pinus banksiana* Lamb.) and White Spruce (*Picea glauca* (Moench) Voss) Logs From a Nelder Type Plantation", Canadian Journal of Forest Research, vol. 47, No. 7, 2017, pp. 910-915.

Cool, J., et al., "Knot Detection In Coarse Resolution CT Images of Logs", In 23rd International Wood Machining Seminar, Warsaw, Poland, May 28-31, 2017, pp. 1-9.

Longuetaud, F., et al., "Automatic Knot Detection and Measurements From X-Ray CTM Images of Wood: A Review and Validation of an Improved Algorithm on Softwood Samples", Computers and Electronics in Agriculture, Elsevier, 2012, vol. 85, pp. 77-89.

Li, P., et al., "Labeling Defects In CT Images of Hardwood Logs With Species-Dependent and Species-Independent Classifiers", Proceedings of the IAPR TC-8 Workshop on Machine Perception Applications Technical University Graz, Austria, Sep. 2-3, 1996; pp. 113-126.

Schmoldt, D., et al., "Log Defect Recognition Using CT Images and Neural Net Classifiers", 2nd International Workshop/Seminar on Scanning Technology and Image Processing on Wood, Skellefteå, Sweden; Aug. 14-16, 1995, pp. 77-87.

Oja, J., Evaluation of Knot Parameters Measured Automatically in CT-Images of Norway Spruce (*Picea Abies* (L.) Karst.), European Journal of Wood and Wood Products, vol. 58, No. 5, 2000, pp. 375-379.

Johannson, E., et al., "Automated Knot Detection For High Speed Computed Tomography on *Pinus sylvestris* L., and *Picea abies* (L.) Karst. Using Ellipse Fitting in Concentric Surfaces", Computers and Electronics in Agriculture, vol. 96, 2013, pp. 238-245.

Ballard, D., "Generalizing the Hough Transform to Detect Arbitrary Shapes", Pattern Recognition, vol. 13, No. 2, 1981, pp. 111-122.

Boukadida, H., et al., "PithExtract: A Robust Algorithm For Pith Detection In Computer Tomography Images of Wood—Application to 125 Logs From 17 Tree Species", Computers and Electronics in Agriculture, vol. 85, Jul. 2012, pp. 90-98.

Ronneberger, O., et al., "U-Net: Convolutional Networks for Biomedical Image Segmentation", in International Conference on Medical Image Computing and Computer-Assisted Intervention, Oct. 2015, pp. 234-241.

Schmoldt, Daniel, et al., "Nondestructive Evaluation of Hardwood Logs: CT Scanning, Machine Vision and Data Utilization", Nondestructive Testing Evaluation, vol. 15, 1999, pp. 279-309, XP002531958.

Zhu, Dongping, et al., "A Computer Vision System For Locating And Identifying Internal Log Defects Using CT Imagery", Proceedings, 4th International Conference on Scanning Technology in the Wood Industry, Oct. 28, 1991, pp. 1-13, XP055657360.

\* cited by examiner

COMPUTER IMPLEMENTED METHODS FOR TRAINING OR USING A SOFTWARE INFRASTRUCTURE BASED ON MACHINE LEARNING TECHNIQUES

FIELD OF THE INVENTION

This invention relates both to a computer implemented method for detecting internal characteristics of interest of an object of a predetermined type, which uses a software infrastructure based on machine learning techniques, and which uses, as input data, data obtained from a three-dimensional tomographic inspection of the object of interest, and to the method used for training the software infrastructure.

DESCRIPTION OF RELATED ART

The invention in question was initially developed with reference to the sector of wood processing, with the aim of making increasingly efficient the information technology tools usable for examining the results of a tomographic inspection so as to allow increasingly improved optimisation of the cutting of logs or boards into smaller pieces of wood.

Despite that this invention is applicable in any other sector in which similar requirements exist. In particular this invention may be used relative to any sector in which a product must be divided into smaller parts which are then subjected to quality checks. It may be used relative to processing of the following products:
- animal meat parts: to assess them with a view to using them for making foods such as sausages and salami and cold cooked meats;
- salami and cold cooked meats and sausages: to identify fat, gristle, air bubbles, presence of moulds before or after slicing;
- sliced bread and cheeses: to identify any air bubbles and/or pollutants; and
- stone materials (e.g.: marble): to check for the presence of inclusions and/or internal gaps.

As already indicated, this invention aims to use, as the starting data, exclusively the information which can be obtained from a tomographic inspection of an object.

As is known, tomography is a technology which allows analysis of the internal structure of an object by processing X-ray images acquired from different angles.

Today the main applications of tomography are in the medical sector, for inspecting luggage at airports, for scientific tests and for sample assessments of the quality of industrial production.

One application that has started to spread in recent years is that of non-destructive inspection of the entire production in a predetermined production chain and in particular the possibility of using that inspection to optimise the subsequent processing steps. As indicated at the start of this description, this sector includes applications in the context of wood processing plants (sawmills), and in particular the use of tomography for optimising the cutting of logs for the production of boards.

The development of automatic systems for inspecting and calculating an optimised cutting pattern, requires the availability of software capable of analysing the tomographic images produced, in a precise, fast and fully automated way, and capable of correctly predicting the quality and the characteristics of the by-products (boards) which it will be possible to obtain once the starting material (log) has been processed. The quality of the by-products will depend for example on their internal structure (e.g.: presence or absence of defects such as knots for structural applications of the wood), or on their surface appearance (in the case of "aesthetic" applications of the wood).

It should be noticed that in the context of this invention the terms "tomographic images" and "data obtained from a tomographic inspection" shall be understood to be synonyms and interchangeable, since the tomographic images are the simple graphical reproduction of the data.

Computed tomography for optimising production in sawmills has been in use for several years. The CT Log scanner is a tomographic scanner produced and marketed by the company Microtec S.r.l. with registered office in Bressanone (Italy), which is capable of performing a tomographic scan of logs with speeds of up to 180 m/min, calculating a model of the internal characteristics of each log and optimising the entire subsequent cutting process, based on the characteristics of the raw material and the production requirements of the sawmill (Giudiceandrea, F., Ursella, E., & Vicario, E.—2011, September—. A high speed CT scanner for the sawmill industry. In Proceedings of the 17th international non destructive testing and evaluation of wood symposium—pages 14-16. Sopron, Hungary: University of West Hungary).

Many publications have demonstrated the economic advantage of optimising the cutting process with the use of tomographic images (Rais, A., Ursella, E., Vicario, E., & Giudiceandrea, F. (2017). The use of the first industrial X-ray CT scanner increases the lumber recovery value: case study on visually strength-graded Douglas-fir timber. Annals of forest science, 74(2), 28; Berglund, A., Broman, O., Grönlund, A., & Fredriksson, M. (2013). Improved log rotation using information from a computed tomography scanner. Computers and electronics in agriculture, 90, 152-158; Stangle, S. M., Brüchert, F., Heikkila, A., Usenius, T., Usenius, A., & Sauter, U. H. (2015). Potentially increased sawmill yield from hardwoods using X-ray computed tomography for knot detection. Annals of forest science, 72(1), 57-65).

The problem of automatic detection of the internal characteristics of a log from tomographic images has been covered by many works, particularly for detecting knots (Andreu, Jean-Philippe, and Alfred Rinnhofer. "Modeling of internal defects in logs for value optimization based on industrial CT scanning." Fifth International Conference on Image Processing and Scanning of Wood. Bad Waltersdorf Austria, 2003; Breinig, L., Brüchert, F., Baumgartner, R., & Sauter, U. H. (2012). Measurement of knot width in CT images of Norway spruce (*Picea abies* [L.] Karst.)—evaluating the accuracy of an image analysis method. Computers and electronics in agriculture, 85, 149-156; Fredriksson, M., Cool, J., Duchesne, I., & Belley, D. (2017). Knot detection in computed tomography images of partially dried jack pine (*Pinus banksiana*) and white spruce (*Picea glauca*) logs from a Nelder type plantation. Canadian Journal of Forest Research, 47(7), 910-915; Cool, J., Fredriksson, M., & Avramidis, S. (2017). Knot detection in coarse resolution CT images of logs. In 23rd International Wood Machining Seminar, Warsaw, Poland, 28-31 May 2017; Longuetaud, F., Mothe, F., Kerautret, B., Krähenbühl, A., Hory, L., Leban, J. M., & Debled-Rennesson, I. (2012). Automatic knot detection and measurements from X-ray CT images of wood: a review and validation of an improved algorithm on softwood samples. Computers and Electronics in Agriculture, 85, 77-89.).

All of these works, although presenting interesting results, highlighted how developing a software capable of correctly interpreting tomographic images is a great challenge which would require the ability to programme a computer in such a way as to be able to differentiate between all possible real cases which may occur.

In an effort to overcome this difficulty the application of machine learning techniques to the study of data obtainable from a tomographic inspection has even been proposed (Pei Li, Jing He, A. Lynn Abbott, & Daniel L. Schmoldt; (1996); Labeling Defects in CT Images of Hardwood Logs With Species-Dependent and Species-Independent Classifiers; Proceedings of the IAPR TC-8 Workshop on Machine Perception Applications Technical University Graz, Austria 2-3 September, 1996; 113-126; Daniel L. Schmoldt, Pei Li, A. Lynn Abbott; (1995), Log Defect Recognition Using CT Images and Neural Net Classifiers 2nd International Workshop/Seminar on Scanning Technology and Image Processing on Wood Skellefteå Sweden, Aug. 14-16, 1995, 77-87). The term machine learning (given its universal use in this invention the English definition is used, corresponding to the Italian term "apprendimento automatico") refers to a set of techniques used to train a computer to autonomously determine information starting from a starting set of data.

As is known, one of the current main applications of machine learning is image recognition. In that context the aim is to autonomously recognise the content of an image. The training is usually based on a mathematical algorithm implemented on a suitable software infrastructure, to which many examples of images labelled based on the criteria of interest are supplied. Part of the examples (known as the training set) is assessed by the algorithm to autonomously calculate a set of internal parameters of the algorithm also using algorithms for optimisation of the result obtained (in this case understood as minimisation of the error).

Once the system has found an optimisation of its own parameters, it is assessed on another group of known examples (called the test set), to check the capacity of the system to operate even in new situations; if the response is favourable, that is to say, if the results are as expected, the system can at last be used at industrial level.

Until a few years ago, machine learning techniques applied to image recognition were only based on a preliminary processing of the images, during which calculation took place of predetermined characteristics on each part of the image (for example gradients, statistical distribution of groups of pixels, SIFT, etc.); the results of the preliminary processing were then passed to a classifier (e.g.: Bayesian, SVN, random forest) previously trained by means of examples (each consisting of input data and corresponding desired output data) to calculate parameters capable of correctly classifying entire images or portions of them.

In contrast, recent years have also seen the spread of so-called deep learning techniques, which use deep neural networks (that is to say, with a number of layers greater than the 2 or 3 present in the past) and in particular convolutional neural networks, which have proved particularly suitable for image analysis. Convolutional Neural Networks—CNN are mathematical algorithms which use as input one or more digital images, and are typically capable of supplying as output a classification of the entire image (e.g.: image of a car, image of a cat, image of the face of a person, etc.), a classification of the single pixels of the image (pixels belonging to the main object of the image—person, car, animal, pixels belonging to the background, to the sky, to the floor, etc.), or a classification of areas of the image which have shared characteristics (e.g.: image division into an area which corresponds to a building, into an area which corresponds to the sky, into an area which corresponds to the floor, etc.—this division of an image into areas which contain pixels that are consistent with each other is defined as semantic segmentation).

Both in literature, and at software level, there are many types of CNN. In many applications CNN are constituted of many successive layers (or levels) of processing. Within each layer it is possible to apply to the input data convolutions with one or more kernels (whose values are learned—decided by the CNN during training), linear or non-linear functions (for example $\max(x,0)$ $\min(x,0)$, etc. where x is the value being examined) or sub-sampling functions. In all of the machine learning applications of interest for this invention, each processing operation involves multiple levels activated one after another, where each level after the first uses as input the output data of the preceding level. Within each level the data are then processed according to various mathematical functions combined according to the choices of the programmer; they may be linear functions, non-linear functions, or combinations of them.

In general, the production of a specialised neural network for a predetermined functionality involves a programmer defining only the so-called "hyperparameters", such as the number of layers, the number of convolutions for each layer, the dimensions and the step of the convolution kernels, and so on. It is also necessary to supply the CNN with a sufficient number of examples in which both the input and desired output are known.

Today many software infrastructures are available which are capable of managing a CNN as well as optimising, during the training step, calculation of the network internal parameters (those used by each function) so that it can perform its task in the best possible way.

In recent years, both the scientific community and many private investors have made enormous investments in this sector, so that today there are various tools which allow both structuring of the software infrastructure of a network, and for its training to be carried out (to make it "learn" the optimum parameters of the network), and perform the so-called inference (use the network to analyse unknown data after the network has been trained).

For example TensorFlow, Caffe.

The main difficulty which arises in the effective use of machine learning systems in general, and of deep neural networks (such as CNN) in particular, is the need to have available an extremely high number of precisely processed examples so that a system is able to correctly learn its own parameters. The number of examples necessary also increases with the complexity of the problem faced.

Whilst to apply classic algorithms to simple enough problems a few hundred examples may be sufficient, the latest generation CNN have demonstrated an ability to solve even very difficult problems, provided that they have available thousands, tens of thousands and sometimes millions of examples to use during the training step.

Until now, to allow the development of networks capable of performing precise image analyses, the main solution adopted has been that involving large numbers of people looking at images and classifying them; in this way in a certain sense it has been possible to teach computers the ability of the human brain in analysing images.

However, in the application of machine learning techniques to interpreting results of a tomographic inspection, although the result of a tomographic inspection may be represented in the form of images (typically images in greyscale representative of the density of the object at each point), it was necessary to face the fact that the images which can be obtained are of a type completely different from those for which the human brain is generally trained.

Indeed, the interpretation of a tomographic image is completely different from that of a normal everyday image, both in terms of its appearance, and the specific fact that it is a three-dimensional image.

In the medical diagnostic sector, a radiologist needs a lengthy learning period before he or she is able to correctly interpret the representation of a tomographic image and typically must pause to look at only a predetermined set of two-dimensional images extracted from the three-dimensional scans (using a computer to produce virtual sections of the tomographic image).

The creation of a database containing a large enough number of tomographic images correctly labelled by human beings therefore proved very complex and time-consuming.

SUMMARY OF THE INVENTION

The innovative insight which forms the basis of this invention was to provide both an innovative method for training a software infrastructure based on machine learning techniques, which allowed the training of software infrastructures for the analysis of data obtained from tomographic inspections, and a corresponding method for creating a large database of examples to be used for the training.

Therefore, in the context described above, the technical purpose of this invention was to provide a computer implemented method for training a software infrastructure, based on machine learning techniques, to analyse data obtained from a three-dimensional tomographic inspection of objects of a predetermined type, with the aim of determining information about internal characteristics of interest of the self-same objects.

The technical purpose of this invention was also to provide a method which would allow the creation of a large database of known examples (for each of which both the result of the tomographic inspection, and the information about the characteristics of interest were known) to be used for training a software infrastructure based on machine learning techniques for analysing tomographic data.

At least some of the technical purposes indicated are achieved by what is described in the appended claims, but the Applicant as of now reserves the possibility of also independently protecting other innovative aspects described in this description, if necessary by filing subsequent divisional applications.

Further features and the advantages of this invention are more apparent in the detailed description with reference to several preferred, non-limiting embodiments of this invention.

BRIEF DESCRIPTION OF THE DRAWINGS

The invention will be better understood and implemented with reference to the attached drawings, which show flow-charts showing the infrastructure of the plant processing step.

DETAILED DESCRIPTION OF PREFERRED EMBODIMENTS OF THE INVENTION

Figure 1:
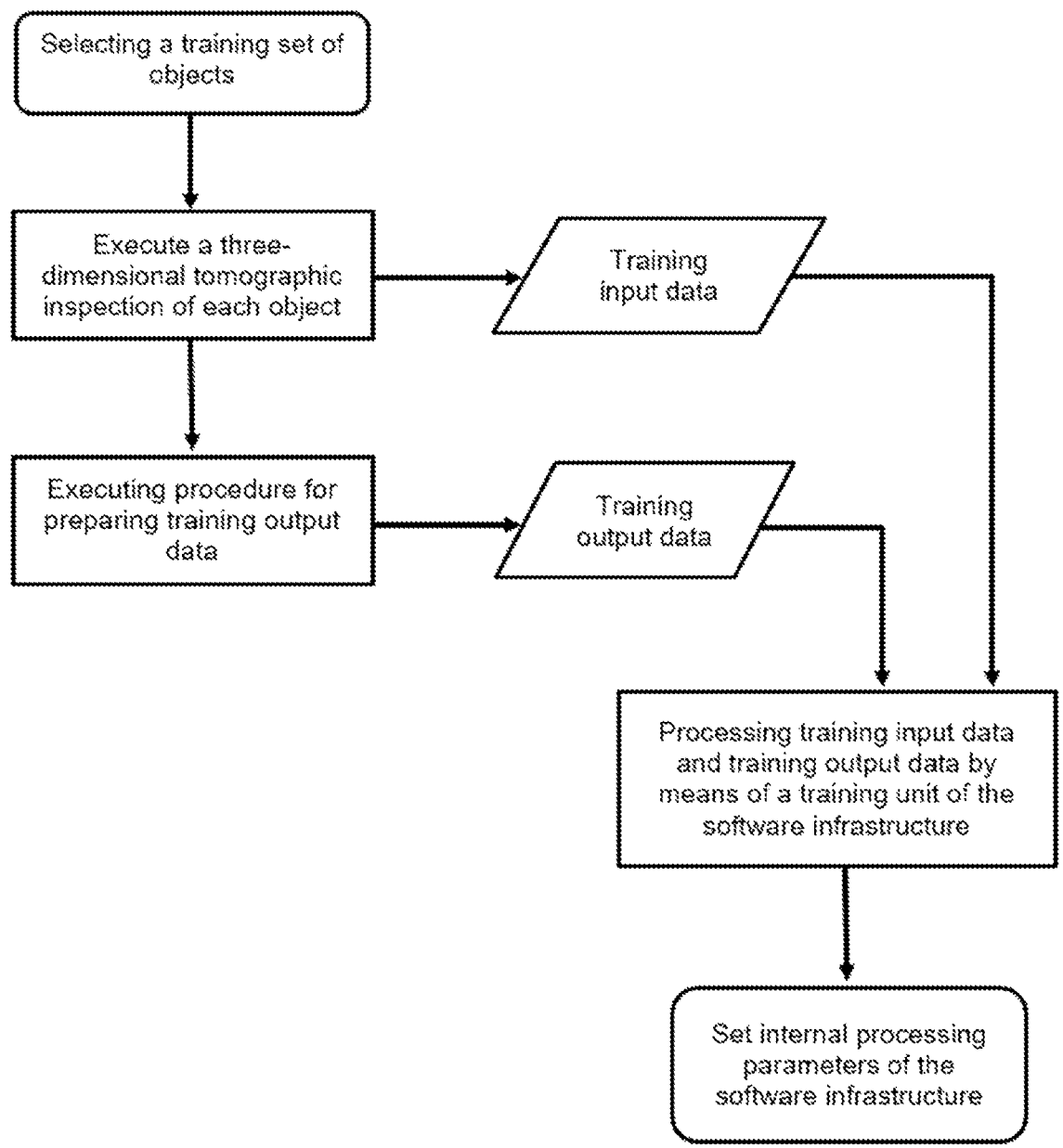
FIG. 1 shows a synthetic flow chart of the whole method for training the software infrastructure.
Figure 2:
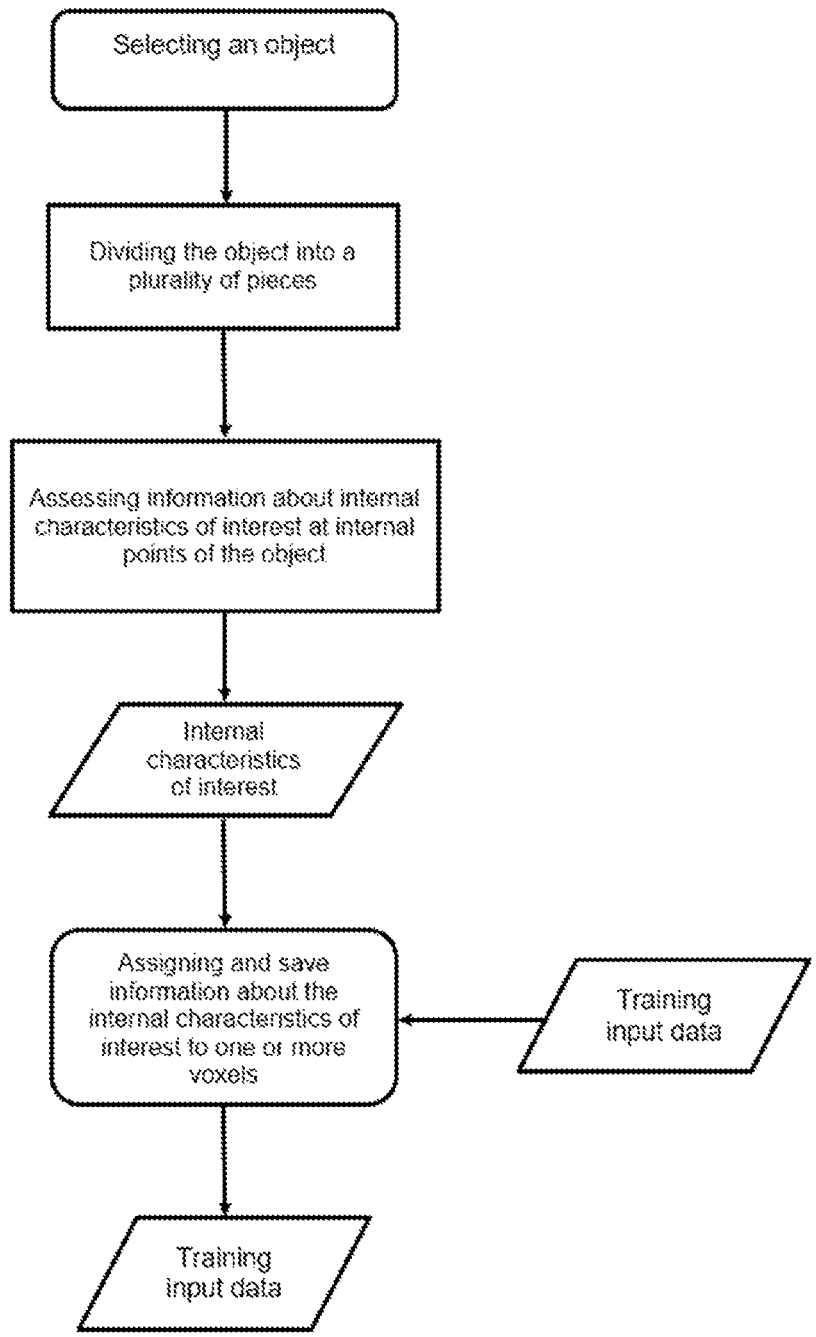
FIG. 2 shows a more detailed flow chart of the procedure for preparing training output data which represents one of the steps in FIG. 1.

As already indicated, this invention was developed in the context of a computer implemented method which allows detection, preferably in a fully automated way, of internal characteristics of interest of an object of a predetermined type. The preferred but non-limiting application of this invention relates to the case in which the objects are logs or boards to be cut into multiple pieces. However, this invention may similarly be implemented for any other type of object which must be cut into multiple pieces in an industrial plant, where the pieces will be subjected to a subsequent automatic quality inspection. For example, they may be food products to be sliced or blocks of stone material to be cut into slabs.

The computer implemented method involves the use of a software infrastructure based on machine learning techniques, preferably a software infrastructure which comprises a neural network, a deep neural network, a convolutional neural network, or a combination of two or more of these.

The software infrastructure is programmed to use, as input data, data obtained from a three-dimensional tomographic inspection of the object. In the known way, the tomographic inspection is performed by virtually dividing, in a computer, the object inspected into a plurality of voxels, that is to say, into a plurality of basic elements of volume, each of which is assumed to have a constant (absolute or relative) density. In a currently preferred application concerning tomographic inspection of logs (the CT Log scanner produced and marketed by the company Microtec S.r.l. with registered office in Bressanone (Italy)), each voxel has a size equal to 1 mm×1 mm transversally to the main axis of extension of the log, and 10 mm parallel to the axis.

The data obtained from the three-dimensional tomographic inspection correspond to a value for each voxel; that value is representative of the average (absolute or relative) density of the object in that voxel, even if it cannot be understood as a precise measurement of the density (it should be remembered that it is obtained by calculating the attenuation of the X-rays attributable to that voxel of material which constitutes the object).

Depending on the embodiments, the software infrastructure may be programmed to supply different types of results.

In a first application, it is programmed to supply as output data, a classification of each voxel (or of at least one set of the voxels into which the object was divided by the tomographic inspection), in a class belonged to. The class belonged to will preferably be selected within a group of preset possible classes belonged to. For example, if the object is a log, for each voxel the data item could correspond to a characteristic of the wood or other material of which it is constituted. The group of possible classes belonged to could therefore include: heartwood, sapwood, sound knot, dead knot, resin sack, crevice/gap, etc. Therefore, in the case of this application, the internal characteristics of interest may be constituted of the nature of what constitutes each voxel.

According to a second application, the software infrastructure may supply, as output data, a segmentation of at least part of the voxels into which the object was divided by the tomographic inspection, into a plurality of volumes each of which is constituted of voxels all classified in the same class belonged to, within a group of preset possible classes belonged to. Using the same example as the preceding case, the output data could be zones/surfaces which delimit the heartwood, the sapwood, the living part of each knot, the dead part of each knot, any resin sacks, any crevices/gaps, etc. Therefore, in the case of this application, the internal characteristics of interest may be constituted of the zones/surfaces of separation between parts of the object which are of a common type.

In contrast, according to a further application, the software infrastructure may be programmed to supply, as output data, one or more three-dimensional groups of spatially adjacent voxels, for each of which the same class belonged to was determined within a group of preset possible classes belonged to.

Again with reference to a log, in this case the output data could be constituted of all of the internal volumes of the log which correspond to one defect in particular, or to any type of defect. In contrast, the voxels which correspond to wood which is free of defects could not be taken into consideration in the output data. For example, the output data could therefore be constituted of all of the internal volumes of the object which are occupied by a knot, or, in other words, of a three-dimensional model of all of the knots of the log. Therefore, in the case of this application, the internal characteristics of interest may be constituted of the internal volumes of the object which share a particular characteristic.

It should also be noticed that depending on how the classes were defined, a specific voxel may even be classified in two or more classes (for example it may be classified both as sapwood and as a knot). In the context of this invention there are also multiple classifications of each knot.

In an evolution of the method being described herein, there may also be, after generation of the output data, a step of processing the output data during which there is determination of the internal characteristics of interest of the object which, in this case, may not directly correspond to the output data. For example, if the output data are constituted of all of the internal volumes of the object which are occupied by a knot, the internal characteristics of interest could be information describing each knot, such as the position along the axis of the log, the volume, the radial extent, the inclination relative to the axis, the taper angle, etc. According to this embodiment of the method, this information may be deduced from the output data by means of successive processing operations on the output data. However, in other embodiments the same information could be obtained directly as output data.

Like all software infrastructures based on machine learning techniques, the one disclosed by this invention also requires, not just preparation of the infrastructure itself according to the common methods of development of this type of software, but also preliminary training of the infrastructure during which the infrastructure gradually optimises its own internal calculation parameters, by analysing, one after another, a large number of examples for which training input data are available, which are qualitatively similar to those which the infrastructure is intended to use once it is fully operational, and training output data, which correspond to the output data which the network should supply once it is fully operational with respect to the training input data supplied to it. It is for this reason that the first innovative aspect of this invention was prepared, which relates to a computer implemented method, for training a software infrastructure based on machine learning techniques, and intended to analyse data obtained from a three-dimensional tomographic inspection of objects of a predetermined type, with the aim of determining information about internal characteristics of interest of the self-same objects.

According to a first embodiment of this method, once a training set comprising a plurality of objects of the same predetermined type (for example logs of the same species) has been selected, for each object the software infrastructure is supplied with training input data and corresponding training output data.

The training input data comprise, for each object, the data obtained from a three-dimensional tomographic inspection of the object.

In contrast, for each object, the training output data comprise information about the internal characteristics of interest assessed at internal points of the object. In connection with the above examples, the following cases are for example possible:
- the internal characteristics of interest are supplied for a plurality of internal points, indicating a class belonged to for each one of them;
- the internal characteristics of interest are supplied only for the internal points which correspond to a specific zone/surface of separation between two zones belonging to different classes;
- the internal characteristics of interest are supplied only for points which belong to a specific class.

Subsequently, processing the training input data and the training output data relative to each object of the training set, the software infrastructure, by means of its own suitably programmed training unit, sets its own internal processing parameters in such a way that there is a correlation between the training input data and the training output data (obviously the correlation will always be there except for a predetermined error considered or defined as acceptable).

Although many training output data (that is to say, information about internal characteristics of interest of the object) may be determined on the basis of a direct examination of the training input data (that is to say, on the basis of an examination of the data obtained from the tomographic inspection of the object), according to this invention, a preferred method was devised for the acquisition of training output data which is not affected by the limits which exist in the interpretation of the tomographic images, described above.

According to this preferred method, the information about the internal characteristics of interest is at least partly assessed at real internal points of the object, after those points have been made accessible by cutting or breaking the object. It should be noticed that in the context of this description the indication that the real internal points are made accessible means that they must be either visibly observable or directly analysable with other inspection techniques (applicable thanks to the fact that the cut or break was made in the object).

Although it is possible to make the internal points accessible even by only making holes in the object, the preferred embodiment of this invention advantageously comprises the cutting or breaking of the object dividing it into two or more pieces.

In the preferred embodiment, after division of the object into two or more parts the real internal points of the object are each positioned on an external surface of one of the pieces of the object which are obtained.

In contrast, in another embodiment, after division of the object into two or more parts, the real internal points of the object may also be positioned inside the respective part of the object, provided that their characteristics of interest can be determined with good precision by an inspection of the respective part of the object.

Advantageously, once the internal points have been made accessible, according to this innovative aspect of this invention, the information about the internal characteristics of interest is obtained by means of an inspection of the piece on which each point is positioned, and in particular of its external surface if the real internal points of interest of the object are positioned on that external surface.

Depending on requirements, the inspection of each real point may be performed in many different ways, but preferably always automatically.

In the case of real internal points which are positioned on the external surface of the relative piece of the object, in one embodiment the inspection may be carried out by observing the surface on which the point is located, in the visible light band, preferably with an RGB camera, in greyscale or with a different number of channels. However, in other embodiments, other inspection techniques may also be used, such as a device which uses the tracheid effect to determine the trend of wood fibres, laser scanners, spectrographic analyses in various visible, infra-red or ultraviolet bands, etc.

In contrast, if the real internal points are positioned inside the piece of the object, the preferred inspection technique is radiographic inspection; this technique proves useful above all in the case of pieces obtained from division of the object, which have a relatively small thickness.

More details about the method for preparation of the training output data, particularly with reference to acquisition of the information about the internal characteristics of interest of real internal points previously made accessible, will be supplied below with reference to a further innovative aspect of this invention.

As already indicated, according to this invention, at least part of the information about the internal characteristics of interest is assessed at real internal points of the object after the latter have been made accessible.

Although it is possible to base the training output data exclusively on information about the internal characteristics of interest assessed at real internal points of the object previously made accessible, in the preferred embodiment of this invention, in order to increase the data usable for training, information about the internal characteristics of interest assessed at internal points of the object which can be deduced in the known way directly from the results of the tomographic inspection is also used.

Once the information about the internal characteristics of interest has been acquired, according to a first embodiment of the training method disclosed by this invention, the information about the internal characteristics of interest is saved in an electronic memory (in particular during the labelling step described below). In particular, for each internal point at which it was assessed, the information about the internal characteristics of interest is saved in combination with information about the correspondence of the internal point to one or more of the voxels into which the object was divided by the tomographic inspection.

Alternatively, in a different embodiment, at least for the characteristics assessed for real internal points previously made accessible, first a spatial correspondence is established between each real internal point of the object considered and one of the voxels into which the object was divided by the tomographic inspection, and the information about the internal characteristics of interest is saved in the electronic memory directly in combination with the corresponding voxel (that is to say, the voxel with which the spatial correspondence was determined). In this case, at the end of preparation of the training output data, the training output data are constituted of a set of labelled tomographic data.

In a different embodiment, the internal characteristics of interest (assessed at each internal point) are saved in the electronic memory in combination with one or more pixels of a digital training image which shows the external surface of the piece of the object. In this case, the output data will have to be furnished with information about the correspondence of each internal point inspected, to one or more of the voxels. That information will also be saved in the electronic memory. In some embodiments, the training image may be constituted of a simple graphical representation (typically in greyscale) of the data obtained with the tomographic inspection at a specific surface which intersects with the object.

Advantageously, in one embodiment, that is obtained by considering the relative positioning of the external surface visible in the training image (or, rather, of each of its pixels), in the tomographic representation of the object constituted of the three-dimensional set of voxels into which the object was divided by the tomographic inspection.

For example, if the objects are logs, and the cutting step resulted in them being divided into boards, each surface of the boards may be represented as a plane which very precisely intersects with the tomographic representation of the starting log. Knowing the position of that plane relative to the log makes it easy to identify the voxels through which the plane passes and to thereby determine which voxel each pixel of the image of the surface of the board belongs to. In the case of wood processing there are already prior art techniques for establishing the position of a board relative to a log from which the board was obtained. That may be done either using markers or other references applied to the log and which can be found in the board, or by directly inspecting the surface appearance of the board or the internal characteristics of the board as described for example in European patent application No. 19161248.0 in the name of the company Microtec S.r.l. with registered office in Bressanone (Italy). EP 2410328 A1 also describes a method for identifying a piece of wood amongst a plurality of starting pieces of wood.

It should also be remembered that there are also various prior art techniques for establishing a posteriori the correspondence between a board and the log from which it has been obtained. In fact, in many wood processing plants tracking of the boards is common in order to be able to follow them from the moment of cutting onwards. Depending on the plants, the tracking may be of the physical type (the system always knows where each board is) or of the virtual type (the system recognises the board for example using the methods indicated above). Whilst tracking of the boards may be relatively complex because in processing plants it is common for the boards, before the final quality control, to be able to change their feed order multiple times (for example, because they are stored for drying or other purposes), in other sectors, such as industrial slicing of food products, tracking is much simpler because the slices, once they have been created, proceed in an orderly manner and are immediately packaged.

However, as described in more detail below, in order to be able to determine spatial correspondence between each real internal point of the object considered, and one of the voxels into which the object was divided by the tomographic inspection, it is necessary to know both from which starting object each piece was obtained, and to know what was the position of the piece (and of its external surface) inside the starting object.

Concerning the relative positioning of the external surface visible in the training image, in the tomographic representation of the object constituted of the three-dimensional set of voxels into which the object was divided by the tomographic inspection, it should also be noticed that, in some cases, the real cutting plane may not perfectly correspond to the virtual cutting plane estimated when determining the cutting pattern; that occurs for example in the case of logs for which it is difficult to guarantee a precise positioning at the saws, whilst it is more difficult for it to be able to occur for objects with more regular supporting surfaces, such as cants, or food products. In any case there are various prior art (automatic) systems which, starting from the theoretical positioning of the cutting plane, allow a check of the position of the real cutting plane. For example, in addition to the above-mentioned techniques (for example the technique described in European patent application No. 19161248.0, having established the correspondence also allows assessment of any offsets between the real board and the virtual board), it is possible to have a check of rotation of the log at the moment of cutting relative to the theoretical angular orientation, or it is possible to have a check on the cant even in this case so as to understand its real orientation relative to the theoretical one.

Now returning to preliminary preparation of the training output data starting from real internal points of the object previously made accessible by cutting or breaking the object, a further innovative aspect of this invention relates to the relative procedure for preparing these training output data to be used in the computer implemented training method described above, some of whose characteristics have already been covered in the preceding paragraphs.

In its most general definition, the procedure for preparing the training output data involves first, after the training input data of an object have been obtained, a dividing step in which the object is divided into a plurality of pieces.

The dividing step is carried out in such a way that each piece obtained has an external surface at least partly constituted of portions of material which before the division were inside the object. Advantageously, if possible, the dividing step is carried out in such a way as to maximise the extent of the surfaces which correspond to internal parts of the starting object. In the case of logs this result is obtained by cutting the log with cutting planes substantially parallel to the main line of extension of the log, or with cutting planes perpendicular to the axis of the log. The closer the cutting planes are, the better.

The procedure for preparing the training output data then involves a labelling step during which information about the internal characteristics of interest of the object at voxels which correspond to portions of the object which lie on the external surface is saved in an electronic memory.

As already described above, during the labelling step it is necessary to establish a correspondence between the points of each piece inspected and the voxels of the tomographic scan of the object from which the piece was obtained.

Therefore, for that purpose, it is essential to know from which object each piece was obtained, and what was the position of the piece inside the object.

Therefore, if that information is not already available, for each piece the labelling step preferably comprises first a step of identifying the object from which the piece was obtained and a step of identifying the position of the piece inside the object from which it was obtained.

In order to identify the object from which each piece was obtained, in general there may be either a recognition of the piece (for example according to the methods indicated above) or a continuous tracking of the piece inside the plant in which it is processed (for example from the cutting station to the check station in the case of the plant described below).

In contrast, in order to identify the position of the piece inside the object it is possible to virtually compare the piece and the starting object to find the position in which the piece matches a part of the starting object (or, rather, of its tomographic mode), or to virtually compare the piece with a corresponding known virtual piece. The latter alternative refers, for example, to the case in which the starting object has been cut according to a known theoretical cutting pattern, which comprises a plurality of theoretical virtual pieces, and the theoretical virtual piece with which the real piece corresponds is known.

Starting from the comparison between the theoretical virtual piece and the real piece, the software tool may be autonomously capable of calculating how much the real piece deviates from the virtual piece (in rigid motion terms) and, by combining the deviation and the known cutting pattern, can establish the position of the piece inside the starting object. In a further variant, the position of the real piece may be calculated if the cutting pattern and any offsets of the real cutting pattern calculated by inspecting the intermediate cant are known.

In one embodiment, before the labelling step, the method involves a photographic step during which, by means of an electronic device, a digital image is generated of at least one part of the external surface of at least one of the pieces into which the object was divided. Advantageously, a digital image generated in this way, relates to an external surface constituted of portions of material which before the division were inside the object. That does not alter the fact that, in order to have more information to include in the training output data, it is also possible to refer to a digital image of surfaces which correspond to external surfaces of the starting object. In the known way, each digital image is constituted of a plurality of pixels.

In a preferred embodiment, the digital image corresponds to a graphical representation of the surface of interest obtained from the tomographic data.

In this case, advantageously, each pixel of the digital image corresponds to a voxel of the tomographic inspection.

In this case, during the labelling step, information about the internal characteristics of interest of the object at each pixel of interest of the digital image is saved in the electronic memory. Depending on the applications, the pixels of interest may be all of those which constitute the digital image, or only a group of them.

In general, the labelling step is advantageously carried out by means of a software tool which, depending on the applications, may adopt various forms.

In a first case provided for, the software tool supplies a graphical interface through which an operator can assign predetermined information about the internal characteristics of interest (for example directly to each voxel or to one or more pixels of the digital image if this is used).

In contrast, in another preferred case, the software is autonomously capable of assigning the information about the internal characteristics of interest to one or more voxels. This case includes the use, in the wood processing sector, of apparatuses already present in many plants, for automatic classification of wooden boards.

In the case of use of a digital image for labelling the internal characteristics, once the information about the internal characteristics of interest has been associated with one or more pixels of the digital image, if a correspondence between each pixel and a voxel is not already preset, the procedure for preparing the training output data may also involve a correlating step, carried out by a computer, during which a spatial correspondence is determined between each pixel with which the information was associated, and one of the of the voxels into which the object was divided by the tomographic inspection.

In other words, the computer determines into which voxel each real point inspected falls. Once the spatial correspondence has been established, the method involves an associating step during which the information about the internal characteristics of interest of the object, saved in association with each pixel, is associated in the electronic memory also (or only) with the corresponding voxel for which the spatial correspondence with the pixel was determined.

Finally, in the definition of the training output data, further data may also be deduced from the real data detected on the real object or on parts of it, for example based on biological type assessments.

A preferred application of this invention is in the context of processing objects of a predetermined type, where the software infrastructure is used to determine the best methods for cutting or for use of each object, starting from the tomographic inspection data of the latter. An example of this type of application is the cutting of logs for the production of boards.

In these cases, the procedure for preparing the training output data may advantageously be carried out, wholly or partly, by one or more management and check computers of a plant for processing the objects of a predetermined type, provided that the plant comprises at least:
   a cutting station in which each object is divided into a plurality of pieces in such a way as to make its internal points accessible; and
   a check station which carries out, advantageously fully autonomously, one or more checks on the pieces obtained by dividing the starting object, for detecting real characteristics of those pieces and their position in each piece.

An example of a check station of this type, in the sector for the production of wooden boards, may be constituted of the apparatus called Goldeneye produced and marketed by the company Microtec S.r.l. with registered office in Bressanone (Italy). The data determined by the check station are made available to the one or more check computers.

In this situation, the real characteristics assessed by the check station are considered to be the internal characteristics of interest according to this invention (meaning, in accordance with this invention, those assessed at real internal points of the object previously made accessible by cutting or breaking the object).

The one or more management and check computers of the plant will then be programmed to combine the information about the characteristics of interest with the tomographic voxels of the starting object; indeed the cutting of the object will be carried out based on a cutting pattern determined starting from the data of a tomographic inspection, where that tomographic inspection may have been carried out in the plant or remotely.

However, advantageously, the plant comprises a tomographic station in which the tomographic scan of each object is carried out; in this way, even the training input data of the object can be obtained by means of the tomographic station.

In an alternative embodiment, which the Applicant reserves the right to protect even independently by filing divisional patent applications, the procedure for preparing training output data is carried out, wholly or partly, by one or more management and check computers of a plant for processing the objects of a predetermined type, where the plant does not comprise the cutting station, but only at least one check station. In this case, it will be possible to divide the objects into pieces in a place different from that in which the quality check takes place (moreover, the cutting place may or may not be the same as the place where the tomographic inspection is performed). In the case of wood, this may occur when, after the boards have been cut in a sawmill, the boards themselves are transferred to a different plant for drying or for special processing operations.

The definition "processing plant" used in the context of this invention therefore advantageously includes both processing plants in which all of the various parts are located in the same place and are physically connected, and processing plants in which the various parts are not physically connected or are even in different places.

According to a further innovative aspect of this invention, the training method may involve an initial training of the software infrastructure at the end of which the software infrastructure may be used with good results in an industrial context, and a subsequent improvement/refinement training, intended to further improve the performance of the software infrastructure. According to the preferred embodiment, the improvement/refinement training is advantageously carried out during the normal use of the software infrastructure and the results of the improvement/refinement training, as soon as they are available, are directly used in the subsequent use.

In particular, the improvement/refinement training may be carried out in a very advantageous way in the context of plants for processing objects of a predetermined type, in which the objects are divided into multiple pieces and in which the quality of the individual pieces is checked (such as those described above). In fact, for each object processed in such plants, the plant supplies both data usable as training input data (the results of the tomographic inspection), and data usable as training output data (the results of the check station).

Therefore, advantageously, the training output data are generated for each object, by the one or more management and check computers of the plant for processing the objects, without interrupting operation of the processing plant, and are then used by the training unit, together with the training input data generated for the same object, for carrying out a further setting of the internal processing parameters of the software infrastructure which correlate the training input data with the training output data; all during normal use of the plant. As already indicated, it is possible that the training output data is generated in a place (production works) different from that in which the objects are cut.

What was just described is an example of application of a more general embodiment of the computer implemented training method according to this invention, which involves an initialising step in which a training set is created which comprises a plurality of objects of a predetermined type, and a plurality of expansion steps during each of which one or more objects of the predetermined type are added to the training set, and in which the training unit processes the training input data and the training output data relative to each object of the training set, for setting internal processing parameters of the software infrastructure which correlate the training input data with the training output data, both after execution of the initialising step, and after execution of each expansion step. In other words, the training of the software infrastructure is repeated after each expansion of the training set, each time taking as the starting parameters those previously determined and executing the new setting only based on the objects added.

As in the example described above, advantageously, the objects added to the training set at each expansion step are objects to which the software infrastructure previously applied the machine learning techniques for analysis of the data obtained from a three-dimensional tomographic inspection of the self-same objects, in order to determine information about the internal characteristics of interest of the self-same objects. This applies for example in the case of boards obtained by cutting logs based on cutting patterns determined starting from processing of the results of the tomographic inspection by the software infrastructure.

Finally, this invention also relates to a plant for processing objects of a predetermined type, and in particular for processing logs, which comprises at least:
- one or more management and check computers (connected to all of the parts of the plant);
- a cutting station in which each object is divided into a plurality of pieces; and
- a check station in which one or more checks are carried out on the pieces obtained by dividing the starting object, to detect real characteristics of those pieces and their position in each piece.

Advantageously the plant also comprises a tomographic station in which the three-dimensional tomographic inspection of each object is carried out, even if it is alternatively possible to use the results of a three-dimensional tomographic inspection previously carried out.

The one or more check computers implement a method for detecting the internal characteristics of interest of each object, which involves the use of a software infrastructure based on machine learning techniques which uses as input data the data obtained from a three-dimensional tomographic inspection of said object. The software infrastructure is also trained with a training method, implemented by means of computer, as described above, and supplies as output data the internal characteristics of interest of the object.

Those internal characteristics of interest of each object supplied by the software infrastructure are then used by the one or more management and check computers to determine a method for cutting each object into the plurality of pieces.

Finally, advantageously, the input data and the data generated by the check station relative to at least some of the objects processed in the plant, are used by the one or more management and check computers to carry out, by means of the training unit, continuous training of the software infrastructure during normal use of the plant (for example according to the methods indicated above).

Finally, it should be noticed that even where the cutting station and the analysis station are located in the same place (works), implementation of this invention does not require the analysis to be performed immediately after the cutting. In fact, in the wood processing sector, it is common for the boards, once cut, to be left to dry for a predetermined time, before undergoing quality checks.

EXAMPLE OF APPLICATION

Below is a description of an example of application which simulates the subject matter of this invention, although it is implemented by manually performing what could be done in a processing line using equipment such as the above-mentioned Goldeneye.

1. Introduction

As indicated in the initial part of this description, automatic detection of the knots of a log from the data of a tomographic inspection has been covered in many works. However, few of these have dealt with the problem of detecting the dead knot surface. The dead knot surface is the surface which divides the part of the knot corresponding to a sound knot from that in which it is a dead knot.

In fact, at the dead part of a knot, a thin layer of bark divides the knot from the rest of the wood; the mechanical resistance of this part is lower, sometimes causing the knot to come out. Therefore, it would be very important to be capable of having a precise estimate of the zone in which there is a border between sound knot and dead knot, to allow optimisation of the cutting model so as to produce higher quality boards. In Oja, J. (2000), Evaluation of knot parameters measured automatically in CT-images of Norway spruce (*Picea abies* (L.) Karst.), European Journal of Wood and Wood Products, 58(5), 375-379, the correlation between the estimated percentage and the measured percentage of sound knots on each board was measured as $R^2=0.72$. In Johansson, E., Johansson, D., Skog, J., & Fredriksson, M. (2013), Automated knot detection for high speed computed tomography on *Pinus sylvestris* L. and *Picea abies* (L.) Karst. using ellipse fitting in concentric surfaces, Computers and electronics in agriculture, 96, 238-245, the border zone was detected by measuring the point where the diameter of the knots stopped increasing. The RMSE value of the estimate of the dead knot surface on pine logs was 12 mm. On the basis of these conditions, two methods according to this invention were applied one after another in an attempt to improve detection of the knots from the tomographic data.

In both cases, a software infrastructure based on convolutional neural networks was used.

In particular, the problem was dealt with by dividing detection of the knots into two steps.

During the first step, the method according to this invention was implemented to carry out a semantic segmentation along the entire axis of the log so as to define the position of each knot.

In the second step, exclusively a zone around each knot was analysed to calculate in general the properties of the knot and, in particular, to identify the dead knot surface.

Therefore, in the first step, the information about the internal characteristics of interest was constituted of the position of the knots along the axis, and more precisely the position and orientation of the axis of the knot.

In contrast, in the second step, the information about the internal characteristics of interest related to the diameter of the knot and the position of the dead knot delimiting surface.

The neural network oriented for semantic segmentation used in the first step is a completely convolutional network which carries out 2D convolutions on consecutive axial section volumes of the log, to produce probability maps which express the probability that each voxel is part of a knot.

In contrast, the network used in the second step aims to classify the volumes of the knots as sound or dead and to identify the correct position of the dead knot surface.

As already indicated, one of the basic requirements for training each software infrastructure based on machine learning techniques is that a large number of input-output examples is supplied to the system.

Labelling of the training output data supplied to the network for the first step was carried out by means of the visual inspection of the tomographic images using a specific interface software.

In contrast, definition of the dead knot surface from the tomographic images was not possible. Therefore, to generate the training output data it was decided that use would be made of measurements taken directly on the surface of boards after they had been obtained by cutting logs.

2 Material and Methods 2.1 First Step: Identification of Each Knot

The tomographic data were generated using a CT Log scanner produced by the company Microtec S.r.l. with registered office in Bressanone (Italy), a scanner which is capable of producing data relative to three-dimensional images in which each voxel has the size 1×1 mm in the transversal direction, and 10 mm along the axis of the log.

Hereinafter in the description x and y will be the two co-ordinates of the tomographic images transversal to a longitudinal axis of the log, and z the third co-ordinate along the axis.

To display and label in 3D each knot directly with reference to the tomographic images, a suitable interface software was developed, in which different views of the same cross-section of the log were presented in the same screen page, to allow labelling of the starting point, the end point, the dead knot surface and the profile of the diameter of the knots. On those images the operator could also define any number of intermediate points along the trajectory of the axis of the knot.

The tomographic images of 75 logs of Scots pine (*Pinus sylvestris*), previously obtained in various sawmills in Europe, were collected in order to create a database. The knots of that log were manually marked with the software previously described, totaling 10,118 knots.

The parametric labelling in each cross-section was converted to produce a volume of voxels corresponding to each log in which each voxel was assigned the value 1 if the voxel belonged to a knot, and the value 0 if not. Each portion of both of the images was resized to have sections with a size of 128×128 pixels for all of the logs, then groups of images were created composed of 5 adjacent sections.

Trained with these data, the neural network was capable of producing, starting from generic input data, a 3D image in which each voxel was substituted by the probability of being part of a knot.

To identify the position and the bounding box of each knot, a special version of the Hough transform was applied (see Ballard, D. H. (1981); Generalizing the Hough transform to detect arbitrary shake; Pattern recognition, 13(2), 111-122).

In the development of the transform a considerable simplification of the model was applied, considering that all of the knots in a log start from the central pith (in fact, epicormic knots are very rare in forests).

The position of the pith along the log can easily be calculated, for example using the algorithm proposed in Boukadida, H., Longuetaud, F., Colin, F., Freyburger, C., Constant, T., Leban, J. M., & Mothe, F. (2012); PithExtract: A robust algorithm for pith detection in computer tomography images of wood—Application to 125 logs from 17 tree species; Computers and electronics in agriculture, 85, 90-98.

In this way it was possible to create a list of xPith (z) and yPith (z) values. Therefore, the axis of a knot was parametrised with 3 parameters:

z-Start, the z co-ordinate of the position where the knot starts;
Orientation, the angle of the direction of the knot in the x, y plane;
Gradient, the inclination of the direction of the knot in the z direction relative to the x y plane.

The algorithm created a 3D Hough map based on the 3 parameters executing the loop on a range of possible Gradient values of between −30% and 30% with a 2% step.

For a given Gradient, for each voxel it is possible to calculate the only position possible in the pith from which an axis of the knot could start so as to pass from the voxel, in such a way that it was possible to create a zStart (x, y, z, Gradient) function, where x, y, z are the position of a generic voxel.

Therefore, it was possible to calculate the orientation of the knot as Orientation (x, y, z)=a $\tan^2$ (yPith (zStart), xPith (zStart)). With these two functions it was possible to calculate for each Gradient and each voxel (identified by the relative x, y, z co-ordinates), the corresponding z-Start and Orientation co-ordinates in the Hough map. Adding the probability value calculated with the convolutional neural network it was possible to calculate the probability of having a knot with the given parameters. Selecting the best local maxima of the map it was possible to define the list of axes of the knots.

2.2 Second Step: Knot Zone Analysis

Identification of the axis of each knot was followed by extraction of a voxel 3D volume which contained the axis.

For each volume extracted the following three reference directions were defined:

radial direction (r): along the orientation of the knot in the x-y plane;
tangential direction (t) orthogonal to directions r and z;
direction z.

The extracted voxel 3D volume was always set to a size of 160×80×80 respectively in directions r, t, z. A different scale factor was applied to the three directions to adapt the knot in space with the maximum resolution allowed.

The scale in direction r was determined by the radius of the log at the given point, the scale in direction t by the estimated maximum diameter, the scale in direction z by the Gradient and by the estimated maximum diameter.

In a first solution tested, the same data used in the first step were used to train a second convolutional neural network which segmented the extracted voxel 3D volumes.

Analysis of the size and of the centre of the voxels segmented along direction r allowed calculation of the direction, the size and the length. The dead knot surface was calculated as the point where the size of the knot stopped increasing along direction r.

However, the results obtained in this way were not satisfactory.

Therefore, it was ascertained that in order to create a neural network with improved performance it was necessary to have available training examples that were more reliable; it was necessary to use as a basis the appearance of the knots on a visible surface, rather than only on tomographic images.

Consequently, thirteen Scots pine logs were first scanned with a CT Log scanner, and then sawed into thin panels with 15 mm thickness.

The knots were manually measured on the surface of the boards. A reference to allow precise determination of the positions of the boards in the starting logs was generated by making several reference holes in the logs, in such a way as to make it possible to calculate the position of a knot in the tomographic image, if the position measured on the board is known and vice versa.

Using the thirteen logs, 2412 knots were measured on the surface of the boards.

In particular, for each knot, as information about the internal characteristics of interest, a record was made of the minimum diameter, the maximum diameter, the position and the sound/dead state. The information about each knot was transferred into the reference system of the specific voxel extracted 3D volume for training the neural network.

One problem encountered is that the information required (dead knot surface and diameter profile) needed a higher resolution of verified information (ground truth) along the radial direction, whilst only a few spaced measurements were available due to the thickness of the boards and their angle relative to the axis of the knot.

Therefore, in an attempt to improve the training of the network the decision was made to extract sub-blocks of eleven slices along direction r, around the positions where real information was available.

Then two different networks were prepared: one for calculating the dead/sound state, the other for calculating the knot diameter.

During training of the network for calculating the sound/dead state it was possible to also extend the information measured to other points of the knot.

In fact, if a knot was detected as sound at a predetermined radial co-ordinate r_alive, for obvious biological reasons the knot was also necessarily sound for all of the other radial co-ordinates less than r_alive. For the same reason, if a knot was detected as dead at a predetermined radial point, all of the subsequent radial sections could be marked as dead.

This allowed the creation of a set of training output data with a large number of samples.

At this point the network was capable of classifying the individual slice of a knot but during the optimisation step it was important to know the dead knot surface, in such a way that it was possible to use a single number to represent the knot state in all of the positions. Therefore, an algorithm was implemented which calculated the inference of the neural network in steps with six sections, defined the point where the state changed from sound to dead and therefore refined the result with stepped inference of a slice around the first hypothesis.

Following calculation of the dead knot surface, system performance was verified by comparing the estimated state with the state of the knots in the sawn boards.

The decision was made to use only the slices of knot where a manual measurement was available as training output data for calculating the diameter. Although interpolation of the diameters measured in two adjacent sections was possible, it was decided that this could have reduced system precision.

As long as it was possible to consider that the branches were not elliptical, the minimum diameter measured on the board was used as the diameter of the knot in the 3D image.

3. Results 3.1 Segmentation of Knots

In order to design and train the networks, a Windows 10 Pro computer was used, and as regards the software infrastructure Keras 2.2.4 with Tensorflow 1.13.1 as the backend.

The first network, intended for semantic segmentation, had a total of 1,962,913 parameters. It followed the U-Net architecture (see Ronneberger, O., Fischer, P., & Brox, T. (2015, October); U-net: Convolutional networks for biomedical image segmentation; In International Conference on Medical image computing and computer-assisted intervention (pp. 234-241). Springer, Cham) with skip connections and convolutional blocks composed of two consecutive convolutional layers.

The first layer interpreted the axis of the channel as a depth axis. Starting from an image size of 128×128 with 5 channels, it compressed the image to size 8×8 with 256 channels at the centre, only to then resize it to 128×128 with a single output class (the probability of part of the pixels of the central section being part of a knot). Each convolutional layer applied 3×3 kernels, and for optimisation the Adam optimiser was used with a learning speed of 0.0002 with binary cross-entropy as a function of predefined loss. Early interruption and reduction of the learning rate on plateau were used during the training process. The inference time for calculation of a 4.2 m long log was 650 ms. All of the calculation times were measured using a computer which uses a RTX 2080 GPU on an Intel Core i7-4770 3.4 GHz processor.

3.2 Dead Knot Border

In total the thirteen logs had 634 knots. Each knot intersected with one or more boards, and the manual measurements were taken at those intersections.

The 634 knots intersected with the boards at 2412 points measured. 1835 knot intersections were randomly selected for training and for the validation set. They generated 34917 knot slices with known dead/sound state and were used for training and validation of the neural network. 577 knot intersections, belonging to 158 knots, were used for the test of the final algorithm in detecting the dead knot surface.

The performance test was carried out by comparing the state of the knots manually measured on the boards with the estimated state based on the estimated dead knot surface. The results are presented in table 1 which shows the sound/dead knot classification confusion matrix.

|      | Estimated |  |
| --- | --- | --- |
| Real | Sound | Dead |
| sound | 301 (88.5%) | 39 (16.4%) |
| dead | 39 (11.4%) | 198 (83.5%) |

The inference of a single portion of the network used for the sound/dead classification required 0.42 ms. Each knot required the inference of a total of 23 knot slices, therefore the total calculation time for the dead knot surface of a knot was 10 ms.

3.3 Knot Diameter

For training and validation of the network, 1776 knot intersections with boards were used (¾ for training and ¼ for validation) whilst 564 were used for the test.

The standard deviation of the difference between the manual measurement and the estimated diameter value was 3.2 mm, the average 0.1 mm.

The inference of a single section of the network for the diameter estimate required 0.58 ms. In total, twelve inferences were used for calculating the diameter along each knot, requiring 6.7 ms per knot.

The total calculation time for a 4.2 m long log with 50 knots was 1450 ms.

The invention described above may be modified and adapted in several ways without thereby departing from the scope of the inventive concept.

All details may be substituted with other technically equivalent elements and the materials used, as well as the shapes and dimensions of the various components, may vary according to requirements.

The invention claimed is:

1. A computer implemented method for training a software infrastructure, the computer implemented method comprising the following steps:
   using one or more computers to implement the method;
   selecting a training set comprising a plurality of objects which are of a same predetermined type;
   once the training set has been selected, for each object of the training set supplying the software infrastructure with training input data and corresponding training output data, for each object of said plurality of objects the training input data comprising data obtained from a three-dimensional tomographic inspection of the object and the training output data comprising information about internal characteristics of interest assessed at internal points of the object, the information about the internal characteristics of interest being at least partly assessed at real internal points of the object, previously made accessible by cutting or breaking the object into two or more separate pieces, the real internal points of the object being each part of one piece of said two or more separate pieces, wherein the software infrastructure is based on machine learning techniques and is configured for analysing, as input data, data obtained from a three-dimensional tomographic inspection of objects, which are of a predetermined type, and for determining, as output data, information about internal characteristics of interest of the objects, the data obtained from the three-dimensional tomographic inspection being constituted of a value at each of a plurality of voxels, into which the object was divided by the tomographic inspection;

processing by means of a training unit of the software infrastructure the training input data and the training output data relative to each object of the training set, for setting internal processing parameters of the software infrastructure which correlate the training input data with the training output data;

the method also comprising a procedure for preparing training output data, said procedure for preparing training output data comprising the following operating steps:

a dividing step in which each object of the training set is divided into a plurality of pieces which are separate, each piece of said plurality of pieces having an external surface at least partly constituted of portions which, before the dividing step, were inside the object, the dividing step being carried out on objects for which the training input data are available; and a labelling step during which a software tool autonomously assigns information about the internal characteristics of interest, at each of said internal points, to one or more voxels which correspond to portions of the object which lie on said external surface and the software tool autonomously saves in an electronic memory said information about the internal characteristics of interest of the object at the voxels into which the object was divided by the tomographic inspection;

wherein the procedure for preparing training output data is carried out by one or more management and check computers of a processing plant for processing objects of said predetermined type during operation of the processing plant, and is carried out using data about the objects processed by the processing plant, the processing plant comprising:

a cutting station in which each object is divided into a plurality of pieces; and a check station in which the processing plant carries out one or more checks on the pieces obtained by dividing each object, to detect real characteristics of said pieces at internal points of the object made accessible by said dividing the object into a plurality of pieces and to detect the position of said real characteristics in each piece; and wherein during the labelling step said real characteristics detected by the processing plant are considered to be said internal characteristics of interest assessed at real internal points of the object.

2. The computer implemented method according to claim 1, wherein, for each piece of said plurality of pieces, the labelling step comprises first a step of identifying the object from which the piece was obtained.

3. The computer implemented method according to claim 2, wherein the step of identifying the object from which the piece was obtained comprises either a recognition of the piece or a tracking of the objects and of the pieces inside the processing plant.

4. The computer implemented method according to claim 2, wherein, for each piece of said plurality of pieces, the labelling step also comprises a step of identifying the position of the piece inside the object from which the piece was obtained.

5. The computer implemented method according to claim 4, wherein the step of identifying the position of the piece inside the object is carried out by virtually comparing the piece and the object from which the piece was obtained, or by virtually comparing the piece with a corresponding known virtual piece.

6. The computer implemented method according to claim 1, wherein each of the real internal points of the object is positioned on an external surface of a piece of said plurality of pieces of the object obtained by cutting or breaking the object, and wherein during the labelling step the information about the internal characteristics of interest is obtained by means of an inspection of that external surface.

7. The computer implemented method according to claim 1, wherein during the labelling step the information about the internal characteristics of interest, at each internal point, is saved in the electronic memory in combination with information about the correspondence of the internal point to one or more of the voxels into which the object was divided by the tomographic inspection, or in combination with a training image which represents the external surface to which the internal point belongs.

8. The computer implemented method according to claim 6, wherein during the labelling step the information about the internal characteristics of interest, at each internal point, is saved in the electronic memory in combination with information about the correspondence of the internal point to one or more of the voxels into which the object was divided by the tomographic inspection, or in combination with a training image which represents the external surface to which the internal point belongs, and wherein information about the correspondence of the internal point to one or more of the voxels, saved in the electronic memory, comprises information about the relative positioning of the external surface visible in the training image, in the tomographic representation of the object constituted of the three-dimensional set of voxels into which the object was divided by the tomographic inspection.

9. The computer implemented method according to claim 1, wherein a spatial correspondence is established between each real internal point of the object considered and one of the voxels into which the object was divided by the tomographic inspection, and wherein during the labelling step the information about the internal characteristics of interest determined at each internal point considered, is saved in the electronic memory in combination with the voxel with which the spatial correspondence was determined, for creating a set of labelled tomographic data which constitute the training output data.

10. The computer implemented method according to claim 1, wherein the procedure for preparing training output data also involves, after the dividing step, a photographic step during which, by means of an electronic device, a digital image is generated of at least one part of the external surface of at least one of the pieces of said plurality of pieces into which the object was divided, the digital image being constituted of a plurality of pixels, and wherein during the labelling step, in combination with each pixel of at least one group of the pixels of the plurality of pixels which constitute the digital image, the software tool saves in the electronic memory information about the internal characteristics of interest of the object at that pixel.

11. The computer implemented method according to claim 10, wherein the procedure for preparing training output data also involves a correlating step carried out by a computer, during which a spatial correspondence is determined between each pixel of said at least one group of pixels of the plurality of pixels of the digital image, and one of the voxels into which the object was divided by the tomographic inspection, and an associating step during which the information about the internal characteristics of interest of the object saved in association with each pixel of said at least one group of pixels, is associated in the electronic memory with the corresponding voxel for which the spatial correspondence with the pixel was determined.

12. The computer implemented method according to claim 1, wherein the entire computer implemented method for training a software infrastructure, is carried out by the one or more management and check computers of the processing plant for processing objects.

13. The computer implemented method according to claim 1, wherein the processing plant also comprises a tomographic station in which the processing plant carries out a tomographic scan of each object, and wherein the procedure for preparing training output data also comprises obtaining the training input data by means of the tomographic station.

14. The computer implemented method according to claim 13, further comprising an improvement/refinement training step carried out during normal use of the processing plant and without interrupting the operation of the processing plant, wherein the output data generated for each processed object by the one or more management and check computers of the processing plant are processed as further training output data by the training unit together with the input data generated for the same object used as further training input data, also for carrying out a further setting of the internal processing parameters of the software infrastructure which correlate the further training input data with the further training output data.

15. The computer implemented method according to claim 1 wherein:
the computer implemented method further includes an initialising step in which a training set is created which comprises a plurality of objects which are of said predetermined type, and a plurality of expansion steps during each of which one or more objects which are of the same predetermined type are added to the training set;
wherein during the step of processing by the training unit, the training unit processes the training input data and the training output data relative to each object of the training set, for setting internal processing parameters of the software infrastructure which correlate the training input data with the training output data, both after execution of the initialising step, and after execution of each expansion step.

16. The computer implemented method according to claim 15 wherein the objects added to the training set in each expansion step are objects to which the software infrastructure previously applied the machine learning techniques for analysis of data obtained from a three-dimensional tomographic inspection of the same objects, in order to determine information about internal characteristics of interest of the same objects.

17. The computer implemented method according to claim 1 wherein the software infrastructure comprises a neural network, a deep neural network, a convolutional neural network, or a combination of two or more of these.

18. A computer implemented method for detecting internal characteristics of interest of an object which is of a predetermined type, the computer implemented method comprising a step of using a software infrastructure based on machine learning techniques, wherein the software infrastructure uses as input data the data obtained from a three-dimensional tomographic inspection of said object, wherein the data obtained from the three-dimensional tomographic inspection correspond to a value at each of a plurality of voxels into which the object was divided by the tomographic inspection, wherein the software infrastructure used is trained with a computer implemented method according to claim 1, and wherein the software infrastructure supplies as output data the internal characteristics of interest of the object.

19. A plant for processing objects which are of a predetermined type, the plant comprising:
one or more management and check computers;
a cutting station in which each object is divided into a plurality of pieces; and
a check station in which the plant carries out one or more checks on the pieces obtained by dividing each object, to detect real characteristics of those pieces and their position in each piece;
and wherein the one or more check computers implement a method according to claim 18, wherein the one or more management and check computers use the internal characteristics of interest of each object which are supplied by the software infrastructure based on the tomographic data of the same object, to determine a method for cutting each object into the plurality of pieces.

20. The plant according to claim 19, wherein the plant also comprises a tomographic station in which the three-dimensional tomographic inspection of each object is carried out.

21. The plant according to claim 19 wherein the input data and the data generated by the check station for at least some of the objects processed are used by the one or more management and check computers to carry out continuous training of the software infrastructure during normal use of the plant.

22. The plant according to claim 19 wherein the one or more management and check computers are also configured to implement a method for training a software infrastructure, wherein:
the software infrastructure is based on machine learning techniques and is configured for analysing, as input data, data obtained from a three-dimensional tomographic inspection of objects, which are of a predetermined type, and for determining, as output data, information about internal characteristics of interest of the objects,
the data obtained from the three-dimensional tomographic inspection being constituted of a value at each of a plurality of voxels, into which the object was divided by the tomographic inspection;
the method for training the software infrastructure comprising the following steps:
selecting a training set comprising a plurality of objects which are of a same predetermined type;

once the training set has been selected, for each object of the training set supplying the software infrastructure with training input data and corresponding training output data, for each object of said plurality of objects the training input data comprising data obtained from a three-dimensional tomographic inspection of the object and the training output data comprising information about internal characteristics of interest assessed at internal points of the object, the information about the internal characteristics of interest being at least partly assessed at real internal points of the object, previously made accessible by cutting or breaking the object into two or more separate pieces, the real internal points of the object being each part of one piece of said two or more separate pieces;

processing by means of a training unit of the software infrastructure the training input data and the training output data relative to each object of the training set, for setting internal processing parameters of the software infrastructure which correlate the training input data with the training output data;

the method also comprising a procedure for preparing training output data, said procedure for preparing training output data comprising the following operating steps:

a dividing step in which each object of the training set is divided into a plurality of pieces which are separate, each piece of said plurality of pieces having an external surface at least partly constituted of portions which, before the dividing step, were inside the object, the dividing step being carried out on objects for which the training input data are available; and a labelling step during which a software tool autonomously assigns information about the internal characteristics of interest, at each of said internal points, to one or more voxels which correspond to portions of the object which lie on said external surface and the software tool autonomously saves in an electronic memory said information about the internal characteristics of interest of the object at the voxels into which the object was divided by the tomographic inspection;

wherein the procedure for preparing training output data is carried out by one or more management and check computers of a processing plant for processing objects of said predetermined type during operation of the processing plant, and is carried out using data about the objects processed by the processing plant, the processing plant comprising:

a cutting station in which each object is divided into a plurality of pieces; and a check station in which the processing plant carries out one or more checks on the pieces obtained by dividing each object, to detect real characteristics of said pieces at internal points of the object made accessible by said dividing the object into a plurality of pieces and to detect the position of said real characteristics in each piece; and wherein during the labelling step said real characteristics detected by the processing plant are considered to be said internal characteristics of interest assessed at real internal points of the object.

* * * * *